US005589356A

United States Patent [19]
Tam

[11] Patent Number: 5,589,356
[45] Date of Patent: Dec. 31, 1996

[54] LITIGATION OF SIDECHAIN UNPROTECTED PEPTIDES VIA A MASKED GLYCOALDEHYDE ESTER AND O,N-ACYL REARRANGEMENT

[75] Inventor: James P. Tam, Nashville, Tenn.

[73] Assignee: Vanderbilt University, Nashville, Tenn.

[21] Appl. No.: 81,412

[22] Filed: Jun. 21, 1993

[51] Int. Cl.[6] .............................. C12P 21/06; C07K 1/00; C07K 1/107
[52] U.S. Cl. .................. 435/68.1; 530/323; 530/339; 530/345; 530/402
[58] Field of Search ................... 530/323, 333, 530/334, 335, 338, 339, 345, 402; 435/68.1

[56] References Cited

U.S. PATENT DOCUMENTS

| 5,118,810 | 6/1992 | Santini | 548/181 |
|---|---|---|---|
| 5,304,631 | 4/1994 | Stewart et al. | 530/323 |

OTHER PUBLICATIONS

Blake, J. "Total Synthesis of S–carbamoylmethyl Bovine Apocytochrome c by Segment Coupling".
Fotouhi, N. "Peptide Synthesis by prior Thiol Capture".
Kemp, D. S. & R. I. Carey "Resolution of the Histidine Problem for Thiol Capture . . . ".
Kemp, D. S. "Peptide Synthesis by Prior Thiol . . . ".
Kemp, D. S. "Peptide Synthesis by Prior Thiol Capture".
Yamashiro "New Segment Synthesis . . . ".
Yamashiro et al. (1988) *Int. J. Pept. Prot. Res.*, 31, 322–334.
Kemp et al. (1986) *J. Org. Chem.*, 51, 3320–3324.
Kemp et al. (1989) *J. Am. Chem. Soc.*, 54, 1589–1603.
Kemp et al. (1991) *Teth. Lett.*, 32(25), 2845–2848.
Fotouhi et al. (1989) *J. Org. Chem.*, 54, 2803–2817.
Blake (1986) *Int. J. Pept. Prot. Res.*, 27, 191–200.
Bognár et al. (1975) *Liebigs Ann. Chem.*, (5), 1637–1657.
Kemp et al, (1989) *J. Org. Chem.*, 54, 3640–3646.
Kwiatkowski et al. (1990) *Tet. Lett*, 31(15), 2093–2096.
Hirsuman et al. (1971) *J. Am. Chem. Soc.*, 93(11), 2746–2754.
Kaiser et al. (1989) *Science*, 243, 187–192.
Bayer (1991) *Angew. Chem. Int. Ed. Eng.*, 30(2) 113–129.
Kent, (1988) *Ann. Rev. Biochem.*, 57, 957–989.
Schnölzer et al. (1992) *Science*, 256, 221–225.
Kitaguchi et al. (1989) *J. Am. Chem. Soc.*, 111, 9272–9273.

Primary Examiner—David M. Naff
Assistant Examiner—Jon P. Weber
Attorney, Agent, or Firm—Klauber & Jackson

[57] ABSTRACT

A method of chemical ligation of peptides that requires no side chain protecting groups and no activation of the C-α carboxyl group is presented. The method consists of three steps. In the first step, initiation, a masked glycoaldehyde ester is enzymatically or chemically coupled to the C-terminal carboxylic acid of an sidechain unprotected first peptide. In the second step, ring formation, the masked aldehyde ester of the first peptide is unmasked, and then reacted with the N-α amino acid of a second sidechain unprotected peptide to form a ring structure. In the third step, rearrangement, the O-acyl ester linkage transfers at higher pH to an N-acyl linkage on the ring to form a peptide bond.

12 Claims, 7 Drawing Sheets

Scheme II.
i. DMF, 60–70°C, 24 h; ii. 30% TFA in $CH_2Cl_2$ (2–5% $H_2O$);
iii. $H_2O/CH_3CN$, pH 2–5; iv. pH 6–9.

FIG. 1

Scheme I

$R_1, R_2$ = peptide chains
R' = H, CH$_3$
X = O, S

FIG. 3

IIIa     IIIb     IIIc

FIG. 2

Scheme II.
i. DMF, 60-70°C, 24 h; ii. 30% TFA in CH$_2$Cl$_2$ (2-5% H$_2$O);
iii. H$_2$O/CH$_3$CN, pH2-5; iv. pH6-9.

Table 1. Rate (t1/2, hr) of the O- to N- Acyl Transfer Reaction

| pH | 5 | 6 | 7 | 7.4 | 8 | 9 |
|---|---|---|---|---|---|---|
| IId 1 to IIe 1 | | 37.5 | 22.2 | 20.2 | 9.9 | 3.4 |
| IId 2 to IIe 2 | | 55 | 8.4 | 9.5 | 11 | 9.3 |

FIG. 8

Abbreviations:

| | | | |
|---|---|---|---|
| Ser | Serine | Z-Ala | Carbobenzoxyalanine |
| His | Histidine | FM | Formyl Methyl Ester |
| Thr | Threonine | TFA | Trifluoroacetic Acid |
| Tyr | Tyrosine | HPLC | High Pressure Liquid Chromatography |
| Cys | Cysteine | NaOH | Sodium Hydroxide |
| Lys | Lysine | NMR | Nuclear Magnetic Resonance |
| Arg | Arginine | Z-Ala-Pro | Carbobenzoxy Alanyl Proline |
| Pro | Proline | X | Any Amino Acid |
| Ile | Isoleucine | ACM | Acetamidomethyl |
| Phe | Phenylalanine | Ala ODMOE | 2-dimethoxyethyl Ester of Alanine |
| Trp | Tryptophan | DMSO | Dimethylsulfoxide |
| Leu | Leucine | DMF | Dimethylformamide |
| Val | Valine | Ala | Alanine |
| Gly | Glycine | | |

LITIGATION OF SIDECHAIN UNPROTECTED PEPTIDES VIA A MASKED GLYCOALDEHYDE ESTER AND O,N-ACYL REARRANGEMENT

This invention was made with government support under grant number AI 28701 from the National Institute of Allergy and Infectious Diseases (NIAID). The United States government has certain rights in the invention.

This invention was made with government support under grant number AI 28701 from the National Institute of Health (NIH). The United States government has certain rights in the invention.

BACKGROUND OF THE INVENTION

The present invention relates to a method for ligating the carboxylic and the amino groups of one or two peptide segments through an amide bond where the functional groups of the segments are either minimally protected, partially protected, globally protected or not protected at all. More particularly, it relates to a method for ligating one peptide segment to itself or two peptide segments to each other by using a masked aldehyde ester incorporated onto the carboxylic group of a first peptide segment through an enzymatic coupling procedure, which masked aldehyde ester is then released in order that it may react with a β-functionalized amino group of a second peptide segment to form a ring leading to an O to N-acyl rearrangement step which results in the formation of an amide bond between the peptide segments.

The synthesis of peptides or proteins has become highly efficient with the advances of the solid-phase peptide synthesis and recombinant DNA technology. Solid-phase peptide synthesis with the aid of automation and other mechanical devices can quickly produce a peptide of greater than 100 amino acids or a library of hundreds of short peptides. The recombinant DNA technology with an optimal expression system can produce proteins accurately and in large quantity. The ideal method of chemical ligation of peptide segments would incorporate both the efficiency of the solid-phase method to generate specific segments and the availability of proteins generated by the recombinant method. The combination of the two types of production of peptide segments would enable engineered proteins to contain unusual structures or nongenetic encoded amino acids by a specific ligation method.

A strong impediment to this approach is a lack of an efficient method for their synthesis. In particular, there is no effective chemical method to selectively couple two unprotected peptide segments to form an amide bond. In general, protecting groups are necessarily attached to nontarget functional groups on the first peptide segment prior to activation of the C-α of the carboxylic group by a coupling reagent and the consequent peptide bond formation with the N-α of the amino group of the second protected peptide segment. As a result, the developments of the various protecting group schemes have been the key for the conventional approach of ligating peptide segments.

However, the use of protected peptide segments is incompatible with the overall scheme of engineering proteins using proteins produced by means of recombinant DNA technology as a source. It also has limitations of being labor-intensive and unpredictable, partly due to the solubility and coupling difficulties of protected peptide segments. Often, large protected peptide segments are minimally soluble in even the most powerful polar aprotic solvents such as dimethylsulfoxide (DMSO) and dimethylforamide (DMF). The problem of insolubility in protected peptide segments has been addressed with limited success in several ways, including the use of (1) partial protecting group strategy which masks all side chains except those of Ser, Thr, and Tyr, and (2) minimal protecting group strategy which masks only thiol and amino side chains. Protecting groups used in all these approaches alter peptide conformations. This creates a difficult problem in the synthesis of large peptides, since folding and renaturation are required after the completion of the synthesis and removal of protecting groups. These limitations, coupled with the ease of obtaining proteins and protein domains through recombinant DNA technologies, have suggested the need to develop a new strategy for ligating unprotected peptides and proteins in order to engineer new proteins with unusual structures, architectures and functions.

Since protecting groups are the root of the problem, scientists have developed two ligation strategies in the past ten years which use unprotected segments. One of the methods requires the use of enzymes in the reverse proteolysis process in conjunction with a high content of water-miscible solvents. Although enzymatic synthesis has been successful with small peptides, enzymatic synthesis of large peptides has presented difficulties. The stringent criteria demanded by using high molar concentrations of peptide segments accompanied by rapid completion of the reverse proteolytic process without the attendant hydrolysis or transpeptidation have been prohibitive obstacles in the enzymatic synthesis of large peptides. Nevertheless, the use of enzymes in coupling unprotected peptide segments eliminates the necessity of activating the carboxylic group involved in the coupling reaction of the peptide segments. Furthermore, it also provides the ability to perform the reaction in an aqueous environment.

Another strategy uses a tricyclic aromatic template containing an aryl alcohol and a thiol to form an active ester with the carboxyl segment and a disulfide with the amino segment, respectively, in order to bring two unprotected peptide segments in close proximity with each other. Such positioning of the peptide segments enables them to undergo an O to N-acyl transfer reaction (Fotouhi, N. et al., 1989; Kemp, D. S. et at., 1991).

A problem with the currently accepted methods of protein synthesis which include both conventional liquid state and solid state peptide syntheses is that their application is limited to small straight chain peptide segments, whereas the need exists for such a method of synthesis to be available for long straight chain peptides, branched straight chain peptides and circular peptides.

It is an object of this invention to provide a method of ligation of two peptide segments from the group comprising, but not limited to, long straight chain peptides, branched straight lo chain peptides and circular peptides, without protecting the various functional groups and without activating the carboxyl group of a first peptide segment which will form a peptide bond with the amino group of a second peptide segment.

In addition, it is an object of this invention to provide a method of ligation of a peptide segment to a compound from the group comprising, but not limited to, DNA by means of incorporating a masked α-aldehyde ester on a carboxylic group and activating that group by releasing the aldehyde thus allowing the carboxylic group to interact with an amino group to form an amide bond. Ligating proteins or peptides to DNA can be useful in biological studies.

It is a further object of this invention that the method developed in this application will make circular proteins readily available for biochemical, biophysical, and therapeutic uses.

Another object of this invention is linking multiple copies of unprotected peptides or proteins to a scaffold or template by an amide to produce a branched protein. This application has broad utility. The present method provides a specific and stable conjugation for peptide/protein antigen to a carder, drug to a protein, reporter group to an antibody or enzyme, and many others.

Furthermore, it is an object of this invention to provide a high effective molarity for peptide bond formation through the efficient O to N-acyl transfer reaction.

It is an additional object of this invention to provide a versatile means of enzymatic coupling to activate a carboxylic group.

Finally, it is an object of this invention that the reactions required in the method of domain ligation may be run in one vessel in aqueous solution, require only pH changes, no intermediate purification steps and no harsh final deprotection, renaturation or disulfide bond formation.

SUMMARY OF THE INVENTION

The present invention relates to a new method to ligate peptide segments chemically without using protecting groups. A major handicap in developing a ligation method using unprotected peptides is that the carboxyl moiety cannot be activated in any form, even as a weak. active ester, in the presence of unprotected side chain amines and other nucleophiles. However, if the N-$\alpha$ and C-$\alpha$ peptide segments can be brought close together, their proximity may enable peptide bond formation through an O to N-acyl rearrangement. The domain ligation strategy takes advantage of the O to N-acyl rearrangement reaction. The strategy consists of four steps consisting of: (1) aldehyde initiation in which a masked glycolaldehyde ester is linked to the carboxylic group of an unprotected peptide by enzymatic reaction; (2) ring formation in which the regenerated aldehyde reacts with the N-a amine of the second unprotected peptide; (3) rearrangement where the O-acyl linkage is transferred to the N-acyl linkage to form a peptide bond at higher pH; (4) reconversion to the natural amino acids if necessary. Only $\alpha$-amino acids which have a 1,2-disubstitution pattern and are able to form a five member ring, and 1,3-disubstituted $\alpha$-amino acids which are able to form a six member ring are able to attain the proper physical spacing which will allow an intramolecular reaction to occur. The chemical ligation method known as domain ligation strategy does not require protecting groups or activation of the carboxyl component in the conventional sense.

The domain ligation strategy can be applied to circular proteins as well as branched straight-chain proteins. These proteins are called circular rather than cyclic because they are connected end to end by a peptide bond while cyclization comprises nonspecific circularization. Circular proteins are difficult synthetic targets because several of them contain three disulfide bonds. However, methods developed for their synthesis would be applicable to most other peptides and proteins. In addition, they have potential therapeutic values and circularization may improve their half life in vivo and increase their stability against proteolytic degradation, particularly by exopeptidases. Unlike cyclic peptides, synthetic circularized proteins are rare because they are not easily susceptible to synthetic methods presently available. One example of a circular protein is BPTI which uses nonspecific carbodiimide for its circularization.

BRIEF DESCRIPTION OF THE DRAWINGS

A. Reaction at pH 9: a. t=22 min; b. t=155 min.; c. t=284 min.; d. t=540 min.

B. Reaction at pH 6: a. t=2.5 h; b. t=11 h; c. t=6 h; d. t=61 h; Peaks 1,2,3 and 4 correspond to compounds Ild1, Z-Ala-OH, Ile1, Ilc1.

FIG. 6 is an HPLC profile for the segment synthesis of the model pentadecapeptide:
  a. before TFA deprotection;
  b. after TFA aleprotection and upon redissolution in acetate buffer (pH 4);
  c. ring formation product after 3 h reaction;
  d. purified ring product before rearrangement;
  e. 20 h at pH 5; and
  f. after 2 days at pH 5.

DESCRIPTION OF THE PREFERRED EMBODIMENT

The present invention provides a method of chemically ligating a first peptide segment to a second peptide segment. The method of ligation has four basic steps: (1) aldehyde initiation in which a masked glycolaldehyde ester is linked to a carboxyl group of a peptide segment by enzymatic reaction; (2) ring formation in which the regenerated aldehyde reacts with the N-$\alpha$ amine of the second tinprotected peptide containing either Cys or Thr to form a thiazolidine or oxazolidine ring, respectively, at relatively acidic pH; (3) rearrangement through an O to N-acyl transfer reaction; (4) reconversion to natural amino acid residues if necessary.

The method of domain ligation brings two unprotected peptides together with unusual regiospecificity through their respective carboxyl and amino functional groups. To achieve this, simple alkyl aldehydes are introduced at the carboxyl terminus of one peptide segment that will then react selectively with the N-$\alpha$ amino group of the second peptide component. The two peptide segments which are to be ligated could comprise opposite ends of the same polypeptide segment, if circularization of the peptide is desired. Ligation of two separate peptide segments will result in a straight chain peptide segment.

Figure 1:
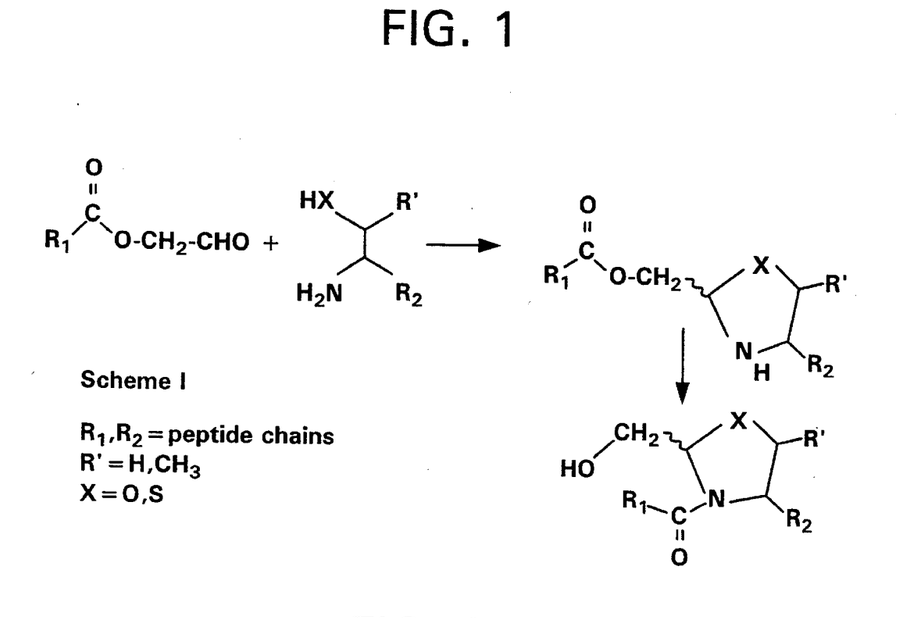
FIG. 1 is a chemical formula representation of the general concept of the method of the present invention.
Figure 2:
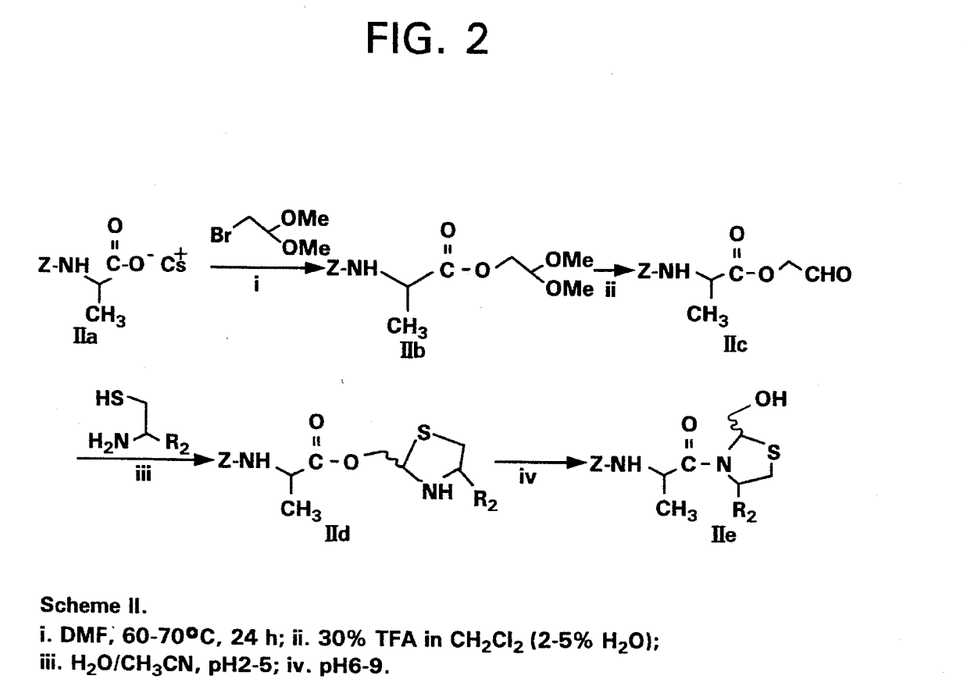
FIG. 2 is a chemical formula representation of an example of the use of the method of the present invention using small compounds.

Aldehydes condense with amines to form imines which are unstable and reversible in aqueous solution unless a ring or conjugated system is formed. The reversibility of the reaction of aldehydes with amines and the stability of ring formation with β-functionalized amines is crucial in the design of this chemical ligation strategy. Side chain amines which do not contain a β-functionalized thiol or hydroxyl group are incapable of ring formation. Specifically, an alkyl aldehyde is introduced via an ester linkage to a carboxyl group of one peptide segment to be captured by the second peptide segment beating a β-functionalized amino-terminal amino group (such as those occurring in Cys, Thr and Ser residues) to form a relatively stable five or six-member ring (FIG. 1). Only α-amino acids which have the 1,2-disubstitution pattern or the 1,3-disubstitution pattern will allow ring formation. Side chain functional groups are not capable of forming the ting. Furthermore, this reaction is usually performed at pH 5 or 6 to further avoid Schiff base formation with side chains of Lys or Arg. The net result is that the carboxyl and amino components are brought together by a ring formation leading to a well positioned and facile intramolecular O to N-acyl rearrangement to form the desired amide bond. Thus, peptide bond formation occurs without activation by a coupling reagent which is an invariable feature of the conventional approach.

The two reacting termini could be from the same peptide if the intention is for circularization. The ester bond which links the peptide segment and the aldehyde is positioned in such a way that an amide bond can then be formed through an intramolecular O to N-acyl transfer reaction (FIG. 1). The domain ligation strategy employs the α-acyloxyacetaldehyde system (a glycolaldehyde ester, or an α-formylmethyl ester of the carboxylic component). In this system the acyl carbonyl and the aldehyde carbonyl are separated by two atoms to facilitate a 5-member ring or by three atoms to facilitate a 6-member ring transition state.

EXAMPLE 1

The initial step of the domain ligation strategy involves the reaction of Z-Ala with a masked acetal containing the aldehyde function (formylmethyl ester, FM) as the carboxyl component which was obtained by reacting the Cs salt of Z-Ala with bromoacetaldehyde dimethyl acetal in DMF. Acetal is particularly suitable because of its ease of removal and it gives an unreactive side product (MeOH) which eliminates the need for a purification process. Treatment with 30% TFA in acetonitrile or the most TFA-compatible organic solvent used in peptide synthesis for acid deprotection, such as $CHCl_3$, $CH_2Cl_2$, $CCl_4$, toluene, etc., in a trace amount of $H_2O$ at 0° C. for 15 to 20 rain smoothly converted the acetal to its aldehyde Z-Ala-OFM. After TFA and the solvents were removed, the aldehyde was allowed to react without purification with β-mercaptoethylamine, cysteine, cysteine methyl ester, or threonine methyl ester to form thiazolidine or oxazolidine, which rearranged to the amide form at higher pH.

The reaction of carbonyl compounds with cysteine involves an initial reaction of sulfhydryl with the carbonyl to give an addition product which condenses with the N-α of the amino group of the cysteine to form a cyclic thiazolidine derivative over a wide range of pH. To avoid the hydrolysis of the ester and the unwanted reaction of aldehyde with the side chain amino groups, the reaction of cysteine or other β-mercaptoamines was conducted with aldehydes at pH 4 to 5. Under these conditions the thiazolidine product was formed almost immediately. At lower pH, this reaction was slower. At pH 2 the reaction required 1–2 hr for completion. The thiazolidines were stable and were easily purified by normal or reversed phase HPLC under usual conditions.

EXAMPLE 2

Figure 7:
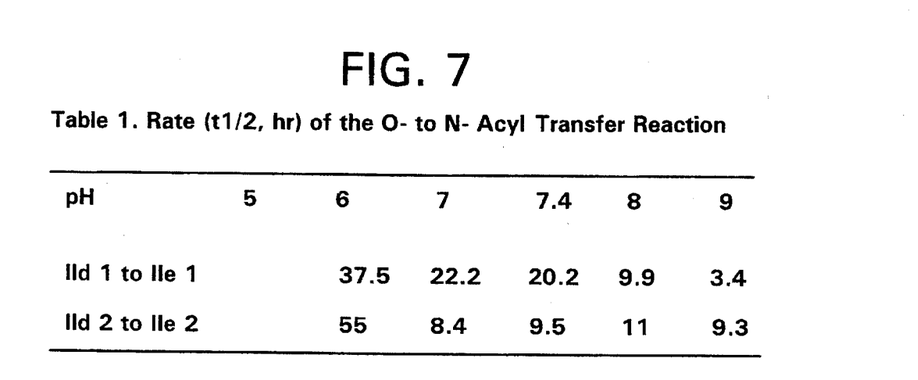
FIG. 7 is a table showing the rate the acyl transfer reaction which occurs during the method of the present invention.
Figure 8:
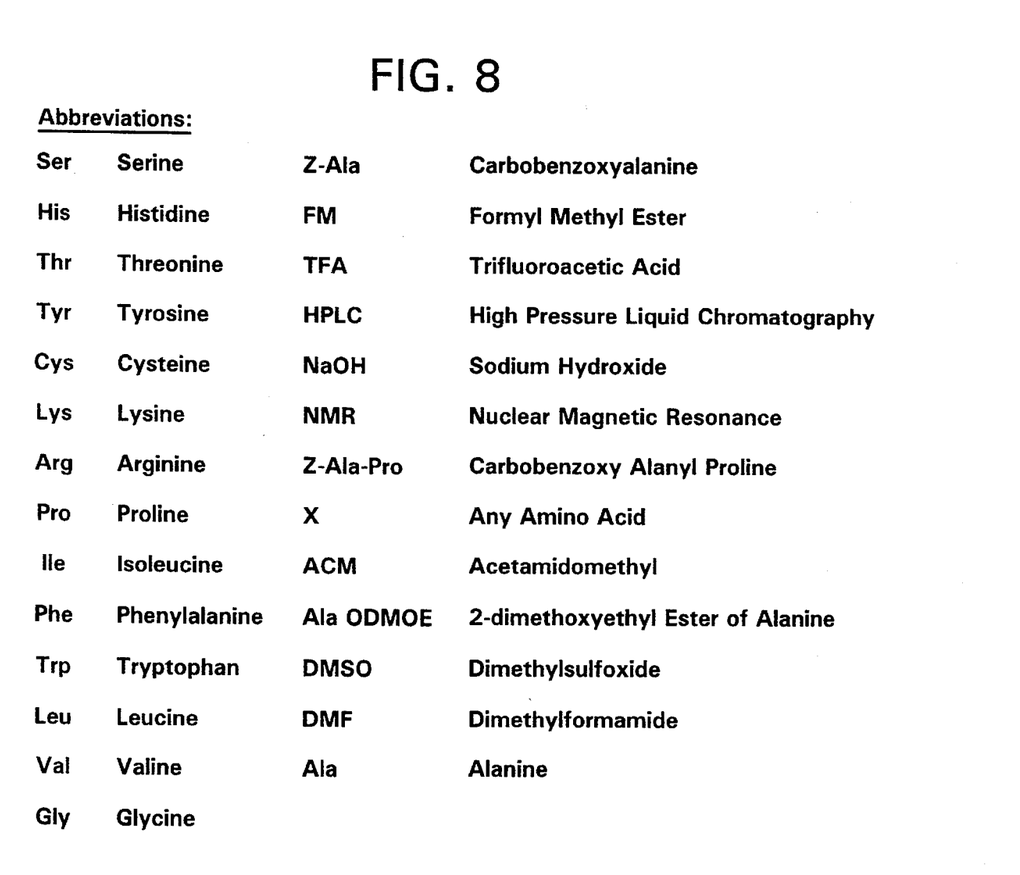
FIG. 8 is a table defining the abbreviated words used in this patent application.

The basic character of the secondary amine in the thiazolidine ring makes it possible for the acyl group to migrate from the ester oxygen to the nitrogen. The O to N-acyl transfer reaction is a dominating side reaction in the acidic deprotection step of peptide synthesis during which the acyl moiety of the peptide migrates from the α-amine to the free hydroxy group on the side chain of a serine or threonine residue. The transfer reaction is reversible upon base treatment involving a 5 member ring oxazolidine-like transition state. FIG. 7 shows that O to N-acyl rearrangement was effective even at the acidic pH range. The weak basicity of the thiazolidine amine (pKa 6.2) may have contributed to this. Rearrangement occurred in all the pH conditions from pH 6 to pH 9. The rate of the reaction was largely dependent on the pH value. As shown in FIG. 7, for IId1 to IIe1, at pH 9, the $t^{1/2}$ for the rearrangement is about 3.4 hr and the reaction proceeds cleanly without any detectable side products, while at pH 6 the $t^{1/2}$ is about one day with some side products probably due to the regenerated aldehyde by slow reversible hydrolysis.

EXAMPLE 3

Both the condensation products and the rearranged products give a mixture of two diastereoisomers due to the creation of a new asymmetric carbon at position 2 of the thiazolidine ring. These diastereoisomers are HPLC separable. The difference between the ester (before rearrangement) and amide (after rearrangement) forms is distinguishable in the following ways: analytically (HPLC), spectrometrically (NMR) and chemically. In the NMR studies, the prominent changes are the disappearance of the proton signals for the secondary ammonium protons in the thiazolidine ring and an up-field shift of two protons on the methylene carbon linked to the oxycarbonyl which, after rearrangement, became an hydroxyl group. The ester form is susceptible to alkali hydrolysis under saponification conditions, whereas the amide form is stable. Treatment of the ester product IId1 with 0.1 to 1N NaOH gave Z-Ala-OH as the hydrolyzed product along with the rearrangement product in 10 min, while the amide form IIe1 was stable under the same conditions.

The rearrangement product now resembles a Z-Ala-Pro structure with a thiol ether linkage as the isoelectronic replacement of the methylene carbon at position 4 and an hydroxymethyl substitution on position 5 of the proline ring. Such modifications will unlikely change the backbone conformation of a proline-containing peptide chain. Thus, this pseudo X-Pro bond can generally be viewed as a substituent for any of the X-Pro bonds present in protein sequences and further enlarges the scope of application of the domain ligation strategy. The N-acyl thiazolidine structure is similar in structure to an acetamidomethyl protected form (Acm-like) of the cysteine residue, and can be reverted to the thiol to form a disulfide by the usual oxidative cleavage method.

EXAMPLE 4

The activation step whereby the formylmethyl ester is introduced to the unprotected peptide segment is an essential element of this method of peptide ligation. With synthetic peptides, this should not pose a problem, since new resins have been developed to give such a linker functional group containing a formylmethyl ester at the carboxyl moiety. For proteins derived from recombinant DNA or natural sources, an activation step is needed. The key is the introduction of the masked aldehyde function onto the carboxylic group of the first component by using the specificity of an enzyme.

Figure 4:
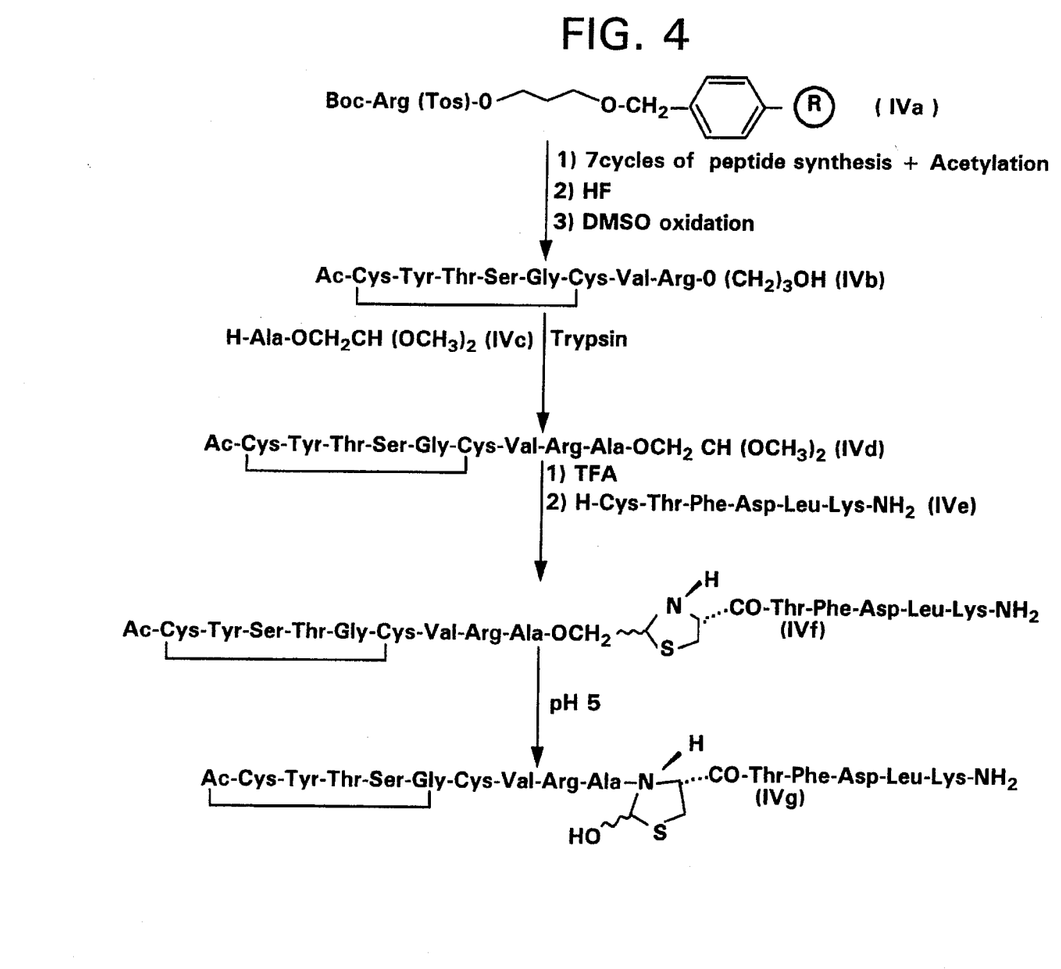
FIG. 4 is a chemical formula representation of an example of the domain ligation method of the present invention, specifically showing the synthesis of a pentadecapeptide (SEQ ID NO:1).
Figure 5A:
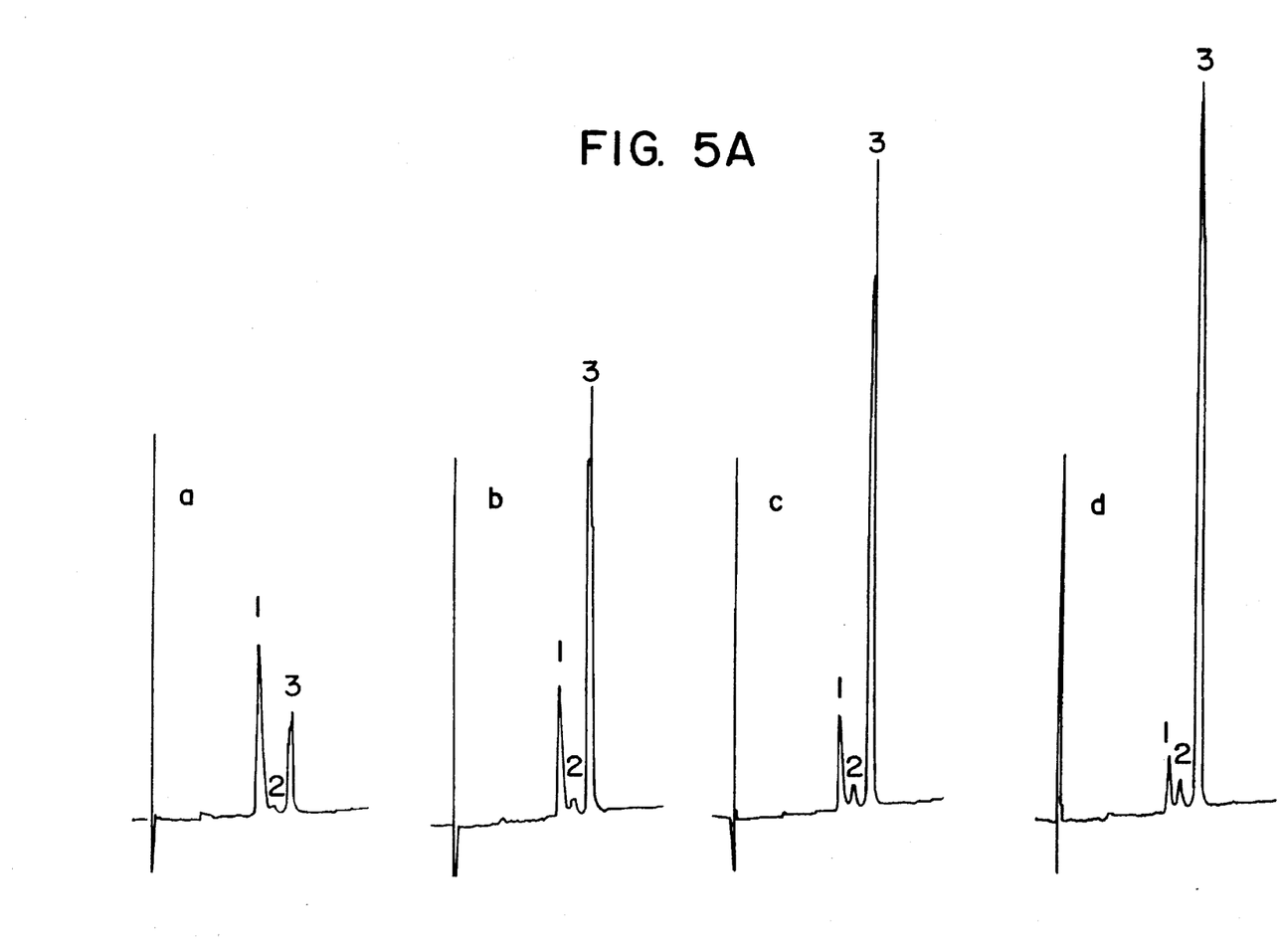
FIGS. 5A and 5B are HPLC profiles of the rearrangement reaction step of the method of the present invention from compound Ild1 to Ile1 as shown on FIG. 2. under the following conditions.
Figure 5B:
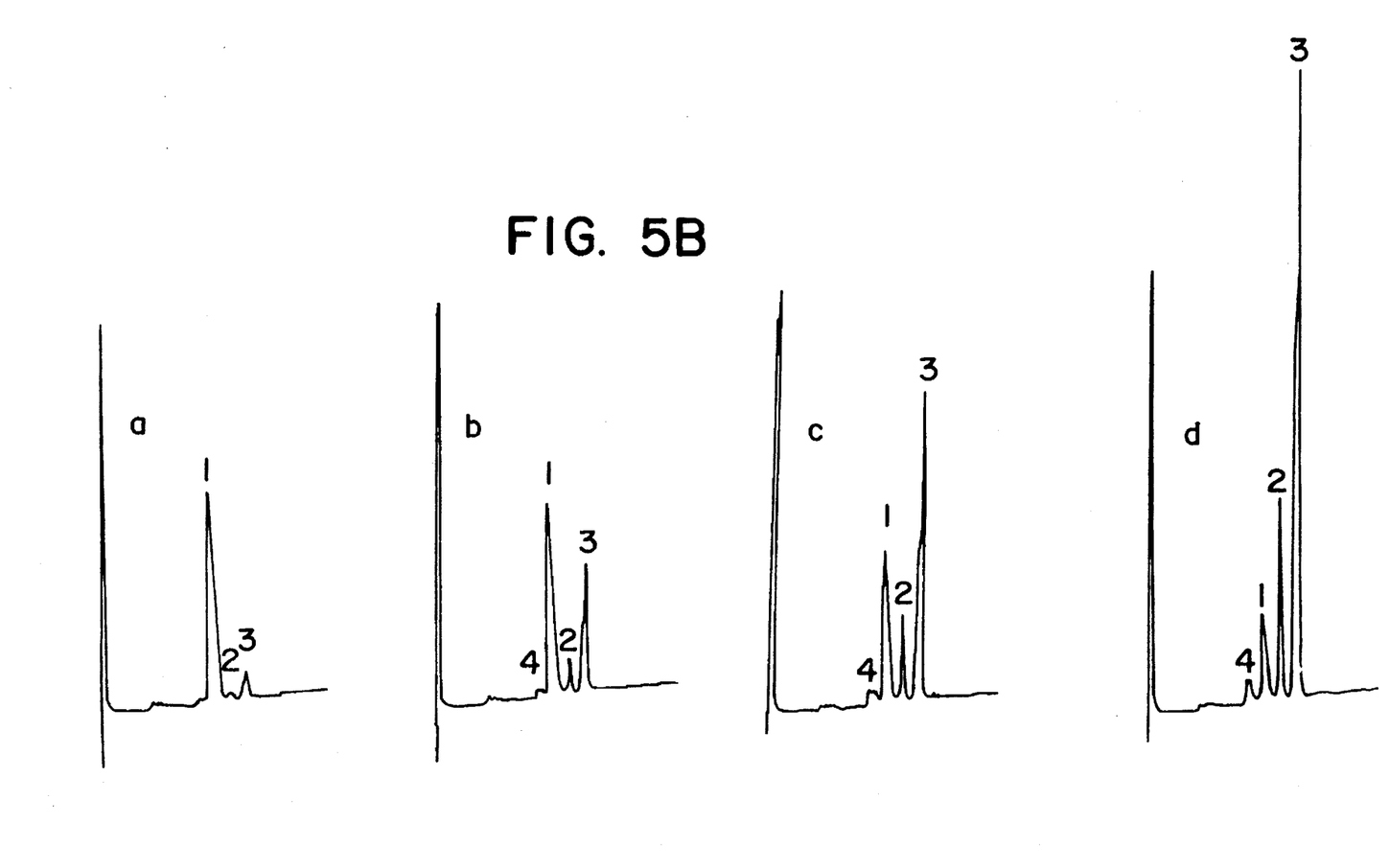
Figure 6:
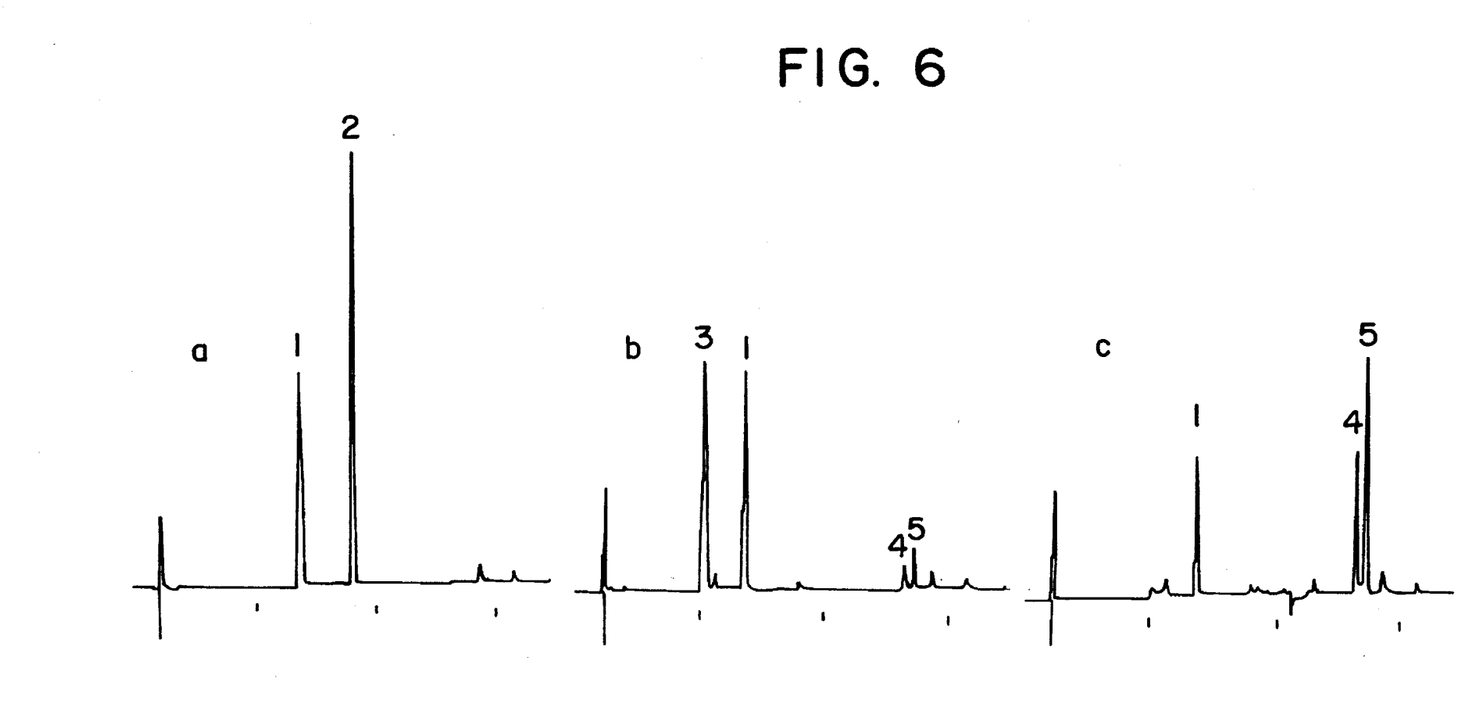

Kinetically controlled aminolysis by enzymes of a peptide ester in the presence of a water miscible organic solvent could be smoothly and efficiently accomplished if a high concentration of the amino component is used. In this case, a large excess of dimethoxyethyl ester of alanine was used. The carboxylic component peptide ester was synthesized by solid phase peptide synthesis method using a newly developed resin (see FIG. 4: IVa). After the cleavage and removal of all protecting groups, this resin provided a peptide containing a carboxyl ester (FIG. 4:IVb) (SEQ ID NO:3) which is a good substrate for enzyme catalyzed coupling. The enzymatic coupling between the peptide and the small substrate, the 2,2-dimethoxyethyl ester of alanine, abbreviated AlaODMoE (IVc) was catalyzed by trypsin in 60% or more DMF and completed within a short time (<½ hr) under the condition of high molar concentrations and large excess of the amino component (FIG. 4:IVc). After the enzymatic coupling, the capture and all subsequent steps were carried out in a similar way as described in the model study. The hexapeptide (FIG. 4:IVe) (SEQ ID NO:5) was premixed with the first peptide acetal (FIG. 4:IVd) (SEQ ID NO:4). The deprotection was achieved using 95% TFA containing 5% $H_2O$ for 3–5 min at 0° C. The regenerated aldehyde showed a shorter retention time in reverse phase HPLC. The HPLC did not reveal any detectable hydrolysis of the ester bond. After removal of TFA, the reactants were redissolved in an acetate buffer (pH 4) to allow the capture reaction, which was also monitored by HPLC. The strong affinity between the aldehyde and the β-thiol amino compound makes it possible that the components can be used in a very dilute molar concentration. This is highly desirable since the reaction between macromolecules has to be carried out in a dilute solution due to the large molecular masses of the reactants. Under the present experimental conditions, the concentration of both components is about 5 mM. The expected thiazolidine product formed cleanly without any detectable side reactions. The rearrangement reaction occurred after the solution was adjusted to pH 5 with aqueous acetate buffer.

All the side chain functional groups in both peptides were unprotected, including the ε-amine of lysine and the β-carboxylic acid of aspartic acid residues, which inevitably have to be protected in the conventional segment coupling approach. It is also important to note that the three steps of this method (acetal deprotection, aldehyde capture and acyl transfer) could be conducted in the same reaction vessel, required only pH changes in aqueous solution and no intermediate purification steps were needed. The product formed (FIG. 4:IVg) (SEQ ID NO:1) also did not require renaturation and oxidation to form the disulfide bond. This has simplified the experimental procedure significantly.

The domain ligation strategy for forming a peptide bond between the opposite ends of one unprotected peptide segment or two separate unprotected peptide segments has high selectivity and efficiency and reaction rate, as well as the ability to be conducted under aqueous conditions, all of which are essential elements of a useful chemical ligation method. The domain ligation strategy meets all of these requirements. The unique reactivity of an aldehyde with a β-mercaptoamino compound under acidic conditions makes it unnecessary to protect other functional groups. This reactivity also accomplishes the ligation of two components with a high effective molarity through the efficient O to N-acyl transfer reaction. Furthermore, this rearrangement permits the formation of an amide bond without the participation of an activated carboxylic group.

The N to O-acyl transfer reaction is a common side reaction in peptide synthesis and usually occurs in anhydrous acid treatments to give an ester linkage similar to that formed in domain ligation strategy. This side reaction is reverted back, i.e. the reverse O to N-acyl transfer reaction to give the normal peptide bond, with great efficiency using a base treatment at pH 8–9. The modified Thr (oxazolidine) and Cys (thiazolidine) can be converted to their respective amino acid by treatment with aqueous base.

Some therapeutic applications of this method include production of proteins having unusual architectures. Selected proteins for design are circularized and branched proteins. Target circularized proteins include interleukin-1 receptor antagonist which is currently in clinical trials as a drug to reduce severity of sepsis and arthritis; monitor peptide which is a cholecystokinin-releasing factor and may be useful for treatment of digestive disorders; and defensin which is a broad-spectrum antibiotic with promising activity against AIDS-related pathogens. Target branch proteins will include a malaria vaccine containing the protective antigen derived from merozoite surface protein (MSP-1). This antigen is the most promising vaccine candidate to date.

Domain ligation strategy is a method to link or circularize totally unprotected peptide and protein segments via a peptide bond without activation. This method is well suited for the synthesis of circularized and branched proteins which are inaccessible directly by recombinant DNA methods and are difficult to obtain by the conventional methods of peptide synthesis. The domain ligation strategy employs a combined approach of organic and peptide chemistry in engineering proteins for therapeutic applications.

Circular proteins differ from cyclic proteins because they are connected end-to-end by a peptide bond, while cyclization is a non-specific circularization. These cyclized proteins represent difficult synthetic targets because several of them contain three disulfide bonds. However, methods developed for their synthesis would be applicable to most other peptides and proteins. In addition, they have potential therapeutic values and cirularization may improve their half-life in vivo and increase stability against proteolytic degradation, particularly the exopeptidases. Unlike cyclic peptides, synthetic circularized proteins are rare because they are not easily accessible to methods presently available. One example, BPTI, uses non-specific carbodiimide for its circularization. Thus, methods developed in this application will make these circular proteins readily available for biochemical, biophysical, and therapeutic evaluations. Furthermore, the domain ligation strategy can be extended and amplified to other applications, such as ligating proteins or peptides with DNA for biological studies.

Another application of the domain ligation strategy is linking multiple copies of unprotected peptides or proteins to a scaffold or template by an amide to produce a branched protein. This application has broad utility and this method would provide a specific and stable conjugation for peptide/protein antigen to a carrier, drug to a protein, reporter group to an antibody or enzyme, and many others.

EXAMPLE 5

A method to study this reaction with all possible combinations of N-terminal amino acids and their side chain functionalities using a library of 400 dipeptides consisting of 20 genetically coded amino acids was employed. To this end, identical copies of a library of 400 dipeptides anchored on cellulose paper were synthesized and an alanyl ester aldehyde was allowed to react with each library under various conditions. The paper support used in these experiments served both as the solid support on which the 400 peptides were synthesized and as a monitoring device on which the ring formation could be observed.

The library was synthesized on Whatman paper using the Fmoc chemistry. The arrangement of the library was in a matrix system containing 400 spots, each representing a dipeptide. The reactivity of each dipeptide towards the aldehyde could be visualized as either a horizontal row which showed the N-terminal amino acid was reactive (e.g. Cys-X, where X represents 20 amino acids) or a vertical column which indicated that the side chains of the carboxyl terminal amino acids (e.g. X-Cys) were reactive. Furthermore, the subsequent O to N-acyl rearrangement could also be observed efficiently by changing to basic buffers or solvents under which the ester bond will be hydrolyzed and the O to N-acyl transferred product would be stable.

For the library to work efficiently, a reporter molecule on the amino acid alkyl ester aldedyde would be required to provide detection of the bimolecular reaction between the aldehyde and the dipeptides. We selected dye-labelling as a reporter group because of its high sensitivity for visible detection, stability under normal conditions, and ease of attachment to the amino acids or peptides. The color functional molecule, 2,4-(dimethylamino)phenylazobenzoic acid (Methy Red, Dpab for abbreviation) was introduced to an amino acid derivative through an amide bond which is stable toward acid and base treatments. Depending on the pH of the aqueous buffer, Dpab-amino acids possess intensive orange to red color and are visible on the paper at low concentration.

Three different aldehydes were used and were esterified to Z-Ala with the following alcohols (1) α-formylmethyl (FM) alcohol, (2) β-formylethyl (FE) alcohol, and (3) β,β,β-dimethylformylethyl (DFE) alcohol. The FM ester aldehyde will give a five-member transition state and should be 30 to 100 fold faster than either FE or DFE esters which requires a 6-member transition state in the O to N-acyl transfer reaction. ME ester rearranged approximately 100 fold faster than the hindered DFE ester and 25 fold faster than FE ester. ME ester is the ester of choice.

Six different amino acids (Cys, Thr, Ser, Trp, His and Asn) are known to form ring products with simple alkyl aldehydes, in particular with formaldehyde which has been used industrially for tanning and medically for inactivation of toxins and biological agents. Because the ME ester aldehydes could be viewed as simple alkyl aldehydes, ring formation is expected to a certain extent with these six amino acids.

Dipeptides with N-terminal Cys, Thr, and Ser (Cys-X, Thr-X, and Ser-X; where X is any amino acid) are of major interest because their ring products can be reverted to Cys, Thr, or Ser. Thiazolidine and oxazolidine can be viewed as temporary protecting groups for these amino acids. Further, the relatively common occurrence of these amino acids in proteins makes them convenient points for ligation in our strategy. The two heterocyclic amino acids Trp and His bearing weakly acidic amines are known to react with alkyl aldehydes to form bicyclic compounds. The initial kinetic ring product with the heterocyclic amine would further rearrange to the stable product involving the C-2 carbon and N-α of the amino group. These bicyclic ring products are not reversible to their natural amino acids. Similarly, the side chain amide of Asn is also known to participate in ring formation, usually under forcing conditions.

EXAMPLE 6

Ring formation in both aqueous buffered solutions at pH 5 to 8 and 90% water-miscible organic solvents at pH 7 has been studied. However, the order of reactivity was significantly different in both systems. N-terminal Cys reacted rapidly and completely with all three aldehydes at all pH ranges tested. With the unhindered FM and FE esters, the reaction was completed within 0.5 hr but required 2 hr for completion with the hindered DFE ester. In contrast, the reactivity of Thr was 500 fold slower. Ser was basically non-reactive. In general, the reactivity of the N-terminal amino acids with Dpab-Ala-O-FM could be divided into three groups. First, Cys-X reacted exceptionally fast with Dpab-Ala-OFM in either aqueous or water-miscible organic and water mixtures. The reactions were completed in 0.5 h at pH 5–8 even at a very dilute concentration of $1\times10^{-6}$M. Second, Thr-X, Trp-X and His-X represented a category that reacted 500 to 100,000 fold slower than Cys-X. Their reactivity was highly dependent on concentrations of Dpab-Ala-O-FM, pH, and the neighboring amino acid. Trp-X formed a heterocylic compound in 30–50% in 160 hr at the acidic pH. Furthermore, Trp-X reacted faster than Thr-X when the concentration of Dpab-Ala-O-FM was lower than $5\times10^{-5}$M probably due to the irreversibility of the Trp-X product.

In contrast, the oxazolidine ring and the Schiff base of Thr-X were not stable at the acidic range and only 5–30% of oxazolidines could be observed in 160 hr. At neutral and basic pH, Thr-X reacted faster than Trp-X and 20–60% of oxazolidines could be observed. N-terminal His formed a heterocyclic compound but its formation was slow at pH 5–8 and less than 10% of product was observable in 160 hr. Third, the ring formation with Ser-X and Asn-X was essentially insignificant in aqueous solution. Asn-X reacted very slowly to form the heterocyclic compound. However, in aqueous solution less than 5% of the reaction product could be observed in 160 hr.

β-carboxamide participates in ring formation with alkyl aldehyde. Primary amides such as Asn, Leu-NH$_2$, and AlaNH$_2$ would react with Z-Ala-O-FM to form a heterocyclic compound. Interestingly, Gln-X which would have formed a six-member ring did not react with Dpab-Ala-O-FM probably due to the slow formation of the six-member ring. Similarly, the reaction with Ser was much slower than Thr and never went to significant completion in the aqueous condition because the opened form of Schiff base and hydrolysis were favored.

The neighboring amino acids exert either rate enhancement or retardation in ring formation. When the neighboring group amino acid is hydrophobic such as X-Ile, X-Phe, X-Trp, X-Leu, X-Val, and X-Tyr, ring formation was accelerated when compared with X-Ala and X-Gly. This was particularly evident with those dipeptides containing N-terminal amino acids such as His and Ser which exhibited slow ring formation. In contrast, when the neighboring amino acids are hydrophilic and particularly acidic, such as Asp, Glu and Asn, ring formation is retarded. A possible explanation for the observed result might be the participation of the side chains in assisting the hydrolysis of the ring form to the open form or the Schiff base to the starting material. The rate enhancement of the neighboring amino acids might be due to the hydrophobic interaction of the Dpab which contains two phenyl rings with the hydrophobic sequences.

Except for Cys-X, ring formation in 100% aqueous solutions and in a very dilute concentration of Dpab-Ala-O-FM was slow for Thr-X and Trp-X, and insignificant for His-X, Ser-X and Asn-X. The equilibrium favors the open forms of either the hydroxymethyl derivatives or the Schiff base which forms are hydrolyzed by water to the starting materials. However, the equilibrium would be predicted to favor the closed forms in the absence of water. To accelerate ring formation, we experimented with the use of 90% water-miscible organic solvents such as hindered alcohol (isopropanol) and aprotic polar solvents (DMF and DMSO). The use of these water-miscible organic solvents in high concentrations are necessary for reverse proteolysis and compatible with the scheme of using unprotected peptide segments. Furthermore, water-miscible organic solvent and water have been applied to effect the incorporation of the amino ester aldehyde in the first step of the domain ligation strategy.

When the reaction was performed in 90% water-miscible organic solvent buffered to pH 7 in 10% $H_2O$, alcoholic solvents such as isopropanol did not improve the reaction rates. In contrast, the polar aprotic solvents DMF and DMSO greatly accelerated the reaction rates, particularly for Thr-X (except when X is Asp, Glu, or Asn) to give the oxazolidine ring formation in 20 hr (FIG. 1). The rate acceleration for Ser-X was difficult to quantify since only about 25% of oxazolidine was observable in 30 hr. Nevertheless, it represents an increase of about 10 fold when compared to the 100% aqueous solution. The rate enhancement was also found in the ring formation of Trp-X, His-X and Asn-X, but apparently the formation of thiazolidine and oxazolidine was more favored.

After comparing the steric effect of the carboxyl terminus bearing the OME ester aldehyde it was found that the rates of O to N-acyl transfer reaction greater favors small amino acids with Gly>>Ala>Val. Gly is the preferred C-terminus residue.

When preparing proteins containing multiple disulfide bonds, the stability of the ester during the folding, renaturation and disulfide formation, which are usually performed under basic pH and requires long duration of 2 to 3 days, is a major concern. Under such conditions, the hydrolysis of the ester is likely to occur and would lower the yield of the subsequent reaction. For this reason, a new method of peptide ligation has been developed that allows the renamration, and selective disulfide bond formation for peptides and proteins. The key reagent in this new method was dimethylsulfoxide (DMSO). Facile disulfide bond formation by DMSO in aqueous buffered solutions proceeded across a wide range of pH, from acidic to basic. This result will allow the folding and disulfide oxidation to be performed over an acidic range of 5–6 or near neutral pH of 6–7 where hydrolysis will not be significant. The DMSO oxidation overcame the limitation of the conventional oxidation method using air or mixed disulfide that was applicable only over a narrow basic pH range. The sulfur-sulfur bond reaction by DMSO was selective and no side reactions were observed with nucleophilic amino acids such as Met, Trp, or Tyr. Detailed kinetic studies on a series of monocyclic agonist peptides of/IFGF showed that disulfide formation by 20% DMSO was completed in 0.5 to 4 hr, while similar experiments by air oxidation at basic pH required longer duration and produced incomplete reactions. Facile oxidations by DMSO were observed with the basic and hydrophobic, tricyclic 29-residue human defensin and 78-residue heparin-binding EGF. In contrast, air oxidation at basic pH of these molecules led to extensive precipitation and low yields. DMSO is a versatile and useful oxidizing agent for peptides over a wide range of pH and may be particularly suitable for renaturation and oxidation of proteins at acidic pH of the domain ligation strategy.

EXAMPLE 7

Figure 3:
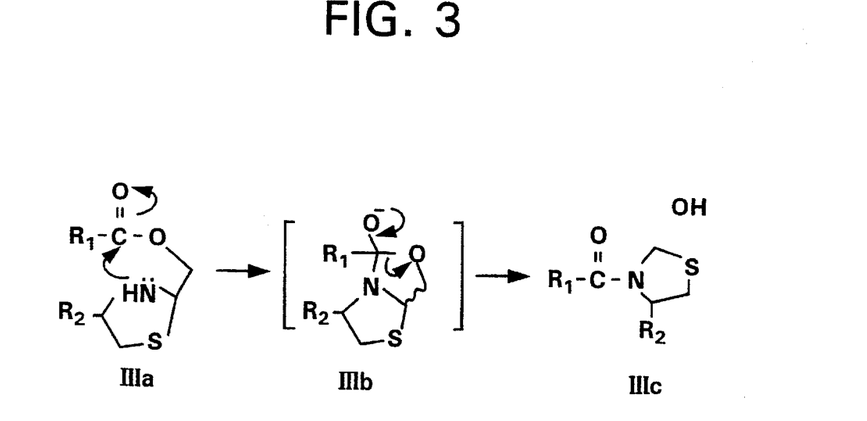
FIG. 3 is a chemical formula representation of the mechanism of the acyl transfer reaction step of the method of the present invention.

TGFα (transforming growth factor-α) is a 50-residue, three-disulfide protein. It contains two domains which are stable structures and we have shown that they can be folded to give the correct disulfide structure. We synthesized two subdomains TGFα1–32 (SEQ ID NO:6) and TGFα33–50 (SEQ ID NO:7) on a new resin (e.g. hydroxyethyloxymethyl resin) by the solid-phase method, refolded, and purified to give an carboxyl-ester and were ligated chemically as shown in FIG. 3. The resulting Thr-33TGFα (SEQ ID NO:2) has the correct molecular weight and the biological activity comparable to TGFα. This synthesis validates the concept of domain ligation strategy and points to its potential of preparing proteins with unusual structures that may not be accessible from recombinant products.

Thus, although there have been described particular embodiments and examples of the present invention, it is not intended that such references be construed as limitations upon the scope of this invention except as set forth in the following claims.

---

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: peptide ( i i i ) HYPOTHETICAL: yes ( v ) FRAGMENT TYPE: entire synthesized peptide ( i x ) FEATURE:
            ( A ) NAME/KEY: a biologically non- significant peptide
                    synthesized for use in demonstration of the domain
                    ligation strategy's effectiveness in the synthesis of
                    proteins
            ( D ) OTHER INFORMATION: a synthetic peptide without specific
                    biological localization or significance ( x ) PUBLICATION INFORMATION:
            ( A ) AUTHORS: Tam, James P
            ( B ) TITLE: A Chemical Ligation Approach to the Synthesis of
                    Proteins Using Unprotected Peptide Segments. Concept and
                    Model Study.
            ( C ) JOURNAL: J. Amer. Chem. Soc. (1993) In press.
            ( K ) RELEVANT RESIDUES IN SEQ ID NO: 1: FROM 9 TO 11

( x i ) SEQUENCE DESCRIPTION: SEQ ID NO:1:

Cys  Tyr  Thr  Ser  Gly  Cys  Val  Arg  Ala  Pro  Thr  Phe  Asp  Leu  Lys
1                   5                        10                       15

( 2 ) INFORMATION FOR SEQ ID NO:2:

( i ) SEQUENCE CHARACTERISTICS:
            ( A ) LENGTH: 50 amino acids
            ( B ) TYPE: amino acid
            ( D ) TOPOLOGY: linear ( i i ) MOLECULE TYPE: protein ( v ) FRAGMENT TYPE: internal fragment ( i x ) FEATURE:
            ( A ) NAME/KEY: Thr-33 TGF alpha
            ( C ) IDENTIFICATION METHOD: Synthesis of the TGF alpha analog
                    in vitro by means of the domain ligation strategy
            ( D ) OTHER INFORMATION: a synthetic analog of TGF alpha
                    produced by means of the domain ligation strategy ( x ) PUBLICATION INFORMATION:
            ( K ) RELEVANT RESIDUES IN SEQ ID NO:2:FROM 32 TO 34

( x i ) SEQUENCE DESCRIPTION: SEQ ID NO:2:

Val  Val  Ser  His  Phe  Asn  Lys  Cys  Pro  Asp  Ser  His  Thr  Gln  Tyr  Cys
1                   5                        10                       15

Phe  His  Gly  Thr  Cys  Arg  Phe  Leu  Val  Gln  Glu  Glu  Lys  Pro  Ala  Cys
               20                       25                       30

Thr  Cys  His  Ser  Gly  Tyr  Val  Gly  Val  Arg  Cys  Glu  His  Ala  Asp  Leu
          35                       40                       45

Leu  Ala
     50

( 2 ) INFORMATION FOR SEQ ID NO: 3:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i i i ) HYPOTHETICAL: yes ( v ) FRAGMENT TYPE: N-terminal fragment ( i x ) FEATURE:
            ( A ) NAME/KEY: a biologically non- significant peptide
                    synthesized for use in demonstration of the domain
                    ligation strategy's effectiveness in the synthesis of proteins
            ( D ) OTHER INFORMATION: a synthetic peptide without specific
                biological localization or significance ( x ) PUBLICATION INFORMATION:
            ( A ) AUTHORS: Tam, James P
            ( B ) TITLE: A Chemical Ligation Approach to the Synthesis of
                Proteins Using Unprotected Peptide Segments. Concept and
                Model Study.
            ( C ) JOURNAL: J. Amer. Chem. Soc. (1993) In press.

( x i ) SEQUENCE DESCRIPTION: SEQ ID NO:3:

Cys Tyr Thr Ser Gly Cys Val Arg
 1               5

( 2 ) INFORMATION FOR SEQ ID NO: 4:

( i ) SEQUENCE CHARACTERISTICS:
            ( A ) LENGTH: 9 amino acids
            ( B ) TYPE: amino acid
            ( D ) TOPOLOGY: linear ( i i ) MOLECULE TYPE: peptide ( i i i ) HYPOTHETICAL: yes ( v ) FRAGMENT TYPE: N-terminal fragment ( i x ) FEATURE:
            ( A ) NAME/KEY: a biologically non- significant peptide
                synthesized for use in demonstration of the domain
                ligation strategy's effectiveness in the synthesis of
                proteins
            ( D ) OTHER INFORMATION: a synthetic peptide without specific
                biological localization or significance ( x ) PUBLICATION INFORMATION:
            ( A ) AUTHORS: Tam, James P
            ( B ) TITLE: A Chemical Ligation Approach to the Synthesis of
                Proteins Using Unprotected Peptide Segments. Concept and
                Model Study.
            ( C ) JOURNAL: J. Amer. Chem. Soc. (1993) In press.
            ( K ) RELEVANT RESIDUES IN SEQ ID NO: In SEQ ID NO: 4: Residue
                No. 9

( x i ) SEQUENCE DESCRIPTION: SEQ ID NO:4:

Cys Tyr Thr Ser Gly Cys Val Arg Ala
 1               5

( 2 ) INFORMATION FOR SEQ ID NO: 5:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i i i ) HYPOTHETICAL: yes ( v ) FRAGMENT TYPE: C-terminal fragment ( i x ) FEATURE:
            ( A ) NAME/KEY: a biologically non- significant peptide
                synthesized for use in demonstration of the domain
                ligation strategy's effectiveness in the synthesis of
                proteins
            ( D ) OTHER INFORMATION: a synthetic peptide without specific
                biological localization or significance ( x ) PUBLICATION INFORMATION:
            ( A ) AUTHORS: Tam, James P
            ( B ) TITLE: A Chemical Ligation Approach to the Synthesis of
                Proteins Using Unprotected Peptide Segments. Concept and
                Model Study.
            ( C ) JOURNAL: J. Amer. Chem. Soc. (1993) In press.

(K) RELEVANT RESIDUES IN SEQ ID NO: In SEQ ID NO:5: Residue
No. 1

(xi) SEQUENCE DESCRIPTION: SEQ ID NO:5:

Thr Phe Asp Leu Lys
1               5

(2) INFORMATION FOR SEQ ID NO:6:

(i) SEQUENCE CHARACTERISTICS:
        (A) LENGTH: 32 amino acids
        (B) TYPE: amino acid
        (D) TOPOLOGY: linear     (ii) MOLECULE TYPE: protein
        (A) DESCRIPTION: a synthetic version of the N-terminal 32
            amino acids of TGF alpha which are employed in the
            domain ligation strategy method of Thr-33 TGF alpha
            synthesis     (iii) HYPOTHETICAL: no     (v) FRAGMENT TYPE: N-terminal fragment     (ix) FEATURE:
        (A) NAME/KEY: TGF alpha analog
        (C) IDENTIFICATION METHOD: Synthesis of the TGF alpha analog
            in vitro by means of the domain ligation strategy
        (D) OTHER INFORMATION: a synthetic analog of TGF alpha
            produced by means of the domain ligation strategy     (x) PUBLICATION INFORMATION:
        (K) RELEVANT RESIDUES IN SEQ ID NO:6:Residue No. 32

(xi) SEQUENCE DESCRIPTION: SEQ ID NO:6:

Val Val Ser His Phe Asn Lys Cys Pro Asp Ser His Thr Gln Tyr Cys
1               5                   10                  15

Phe His Gly Thr Cys Arg Phe Leu Val Gln Glu Glu Lys Pro Ala Cys
            20                  25                  30

(2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear     (ii) MOLECULE TYPE: protein
        (A) DESCRIPTION: a synthetic version of the C-terminal 18
            amino acids of TGF alpha which are employed in the
            domain ligation strategy method of Thr-33 TGF alpha
            synthesis     (iii) HYPOTHETICAL: no     (v) FRAGMENT TYPE: C-terminal fragment     (ix) FEATURE:
        (A) NAME/KEY: TGF alpha analog
        (C) IDENTIFICATION METHOD: Synthesis of the TGF alpha
            analog in vitro by means of the domain ligation
            strategy
        (D) OTHER INFORMATION: a synthetic analog of TGF alpha
            produced by means of the domain ligation strategy     (x) PUBLICATION INFORMATION:
        (K) RELEVANT RESIDUES IN SEQ ID NO:7:Residue No. 1

(xi) SEQUENCE DESCRIPTION: SEQ ID NO:7:

Thr Cys His Ser Gly Tyr Val Gly Val Arg Cys Glu His Ala Asp Leu
1               5                   10                  15
Leu Ala

What is claimed is:

1. A method of chemically ligating a C-terminal carboxylic group or a first peptide and an N-terminal amino group of a second peptide, said method comprising:
   a) introducing a masked aldehyde ester which is a glycolaldehyde ester into said carboxylic group of said first peptide;
   b) converting said masked aldehyde ester to its corresponding free aldehyde ester on said carboxylic group of said first peptide;
   c) reacting said free aldehyde ester with the N-terminal amino group of said second peptide whose amino terminal residue moiety is β-functionalized with —SH, —OH, —CO—NH$_2$, indole or imidazole to form a ring structure with said aldehyde on said first peptide and the N-terminal amino acid of said second peptide; and
   d) intramolecular-acyl rearranging said carboxylic group and said amino group such that said carboxylic group and said amino group form an amide bond.

2. The method according to claim 1, wherein the first peptide is physically separate and unattached from the second peptide.

3. The method according to claim 1 wherein an aldehyde ester is selected from the group consisting of an α-formyl methyl ester, an α-formyl ethyl ester, a β,β,β-dimethyl formyl ethyl ester, and the 2,2-dimethyloxyethyl ester of Gly, Ala or Val.

4. The method according to claim 1, wherein the first peptide and the second peptide are on the same polypeptide.

5. The method according to claim 4, wherein an aldehyde ester is selected from the group consisting of an α-formyl methyl ester, an α-formyl ethyl ester, a β,β,β-dimethyl formyl ethyl ester, and the 2,2-dimethyloxyethyl ester of Gly, Ala, or Val.

6. The method according to claim 1, wherein the masked aldehyde ester is introduced into said carboxylic group by enzymatic coupling or by solution solid phase synthesis.

7. The method according to claim 1, wherein the masked aldehyde ester is introduced into said carboxylic group by enzymatic coupling.

8. The method according to claim 1, wherein said converting and rearranging are effected by changes in pH.

9. The method according to claim 1, wherein said method has no intermediate purification steps.

10. The method according to claim 1, wherein the masked aldehyde ester is introduced to said carboxylic group of said first peptide by:
    a) synthesizing the first peptide so that the first peptide has an ester at its C-terminal carboxylic group; and
    b) enzymatically coupling an amino terminal substrate and the ester of the esterified first peptide to produce the masked aldehyde ester of the carboxylic group;
    wherein said substrate is the 2,2-dimethyoxyethyl ester of Gly, Ala, or Val.

11. The method according to claim 1, wherein the aldehyde of the first peptide reacts with a 1,3-disubstituted α-amino terminal residue of the second peptide to form a 6-member ring having the general structure:

wherein X=S of SH, O of OH, or N of —CONH$_2$, indole or imidazole.

12. The method according to claim 1, wherein the aldehyde of the first peptide reacts with a 1,2-disubstituted α-amino terminal residue of the second peptide to form a 5-member ring having the general structure:

wherein X=S of SH, O of OH, or N of indole or imidazole.

* * * * *

UNITED STATES PATENT AND TRADEMARK OFFICE
CERTIFICATE OF CORRECTION

PATENT NO. : 5,589,356
DATED : December 31, 1996
INVENTOR(S) : James P. Tam

It is certified that error appears in the above-indentified patent and that said Letters Patent is hereby corrected as shown below:

On the title page, item [54] and col. 1, line 1,
IN THE TITLE:

Delete "Litigation" and insert

--Ligation--.

Signed and Sealed this

Fifteenth Day of July, 1997

*Attest:*

*Attesting Officer*

BRUCE LEHMAN

*Commissioner of Patents and Trademarks*